(12) United States Patent  
Ponsardin et al.

(10) Patent No.: US 7,796,251 B2  
(45) Date of Patent: Sep. 14, 2010

(54) METHOD, APPARATUS AND SYSTEM FOR RAPID AND SENSITIVE STANDOFF DETECTION OF SURFACE CONTAMINANTS

(75) Inventors: Patrick Louis Ponsardin, Placitas, NM (US); Christopher Scott Kletecka, Willoughby Hills, OH (US); Jeromy Paul Rezac, Albuquerque, NM (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 489 days.

(21) Appl. No.: 11/688,434

(22) Filed: Mar. 20, 2007

(65) Prior Publication Data

US 2007/0222981 A1  Sep. 27, 2007

Related U.S. Application Data

(60) Provisional application No. 60/784,465, filed on Mar. 22, 2006.

(51) Int. Cl.
*G01J 3/44*      (2006.01)
(52) U.S. Cl. ...................................................... 356/301
(58) Field of Classification Search .................. 356/300, 356/301
See application file for complete search history.

(56) References Cited

U.S. PATENT DOCUMENTS

| | | |
|---|---|---|
| 3,364,727 A | 1/1968 | Heath |
| 4,164,138 A | 8/1979 | Burkhart |
| 4,290,043 A | 9/1981 | Kaplan |

(Continued)

FOREIGN PATENT DOCUMENTS

EP    1182425 A1    2/2002

(Continued)

OTHER PUBLICATIONS

PCT International Search Report and Written Opinion in counterpart International Application No. PCT/US07/064475, dated Jun. 30, 2008.

(Continued)

*Primary Examiner*—Tarifur Chowdhury
*Assistant Examiner*—Abdullahi Nur
(74) *Attorney, Agent, or Firm*—Edell, Shapiro & Finnan, LLC

(57) ABSTRACT

Systems and methods for fast and sensitive standoff surface-hazard detection with high data throughput, high spatial resolution and high degree of pointing flexibility. The system comprises a first hand-held unit that directs an excitation beam onto a surface that is located a distance away from the first unit and an optical subsystem that captures scattered radiation from the surface as a result of the beam of light. The first unit is connected via a link that includes a bundle of optical fibers, to a second unit, called the processing unit. The processing unit comprises a fiber-coupled spectrograph to convert scattered radiation to spectral data, and a processor that analyzes the collected spectral data to detect and/or identify a hazardous substance. The second unit may be contained within a body-wearable housing or apparatus so that the first unit and second unit together form a man-portable detection assembly. In one embodiment, the system can continuously and without interruptions scan a surface from a 1-meter standoff while generating Raman spectral-frames at rates of 25 Hz.

30 Claims, 11 Drawing Sheets

U.S. PATENT DOCUMENTS

| | | | |
|---|---|---|---|
| 4,447,800 A | 5/1984 | Kasuya et al. | |
| 4,555,627 A | 11/1985 | McRae, Jr. | |
| 4,689,052 A | 8/1987 | Ogren et al. | |
| 5,373,160 A | 12/1994 | Taylor | |
| 5,416,321 A | 5/1995 | Sebastian et al. | |
| 5,500,369 A | 3/1996 | Kiplinger | |
| 5,687,093 A | 11/1997 | Long et al. | |
| 5,841,546 A | 11/1998 | Carangelo et al. | |
| 6,026,135 A | 2/2000 | McFee et al. | |
| 6,104,301 A * | 8/2000 | Golden | 340/628 |
| 6,166,744 A | 12/2000 | Jaszlics et al. | |
| 6,732,569 B2 | 5/2004 | Ondov et al. | |
| 6,765,668 B2 | 7/2004 | Gardner, Jr. et al. | |
| 6,777,228 B2 | 8/2004 | Lejeune | |
| 6,788,407 B1 | 9/2004 | Higdon et al. | |
| 6,847,446 B2 | 1/2005 | Shilling | |
| 6,852,527 B2 | 2/2005 | Chan et al. | |
| 6,865,196 B2 | 3/2005 | Dobbs et al. | |
| 6,865,926 B2 | 3/2005 | O'Brien et al. | |
| 6,893,876 B2 | 5/2005 | Perraut et al. | |
| 6,917,423 B2 | 7/2005 | Gardner, Jr. et al. | |
| 6,947,134 B2 | 9/2005 | Chang et al. | |
| 6,949,734 B2 | 9/2005 | Neff et al. | |
| 6,952,945 B2 | 10/2005 | O'Brien | |
| 6,985,818 B1 | 1/2006 | Samuels | |
| 7,009,170 B2 | 3/2006 | Dobbs et al. | |
| 7,012,249 B2 | 3/2006 | Krutchinsky et al. | |
| 7,113,275 B2 | 9/2006 | Gardner, Jr. et al. | |
| 7,271,387 B2 | 9/2007 | Chou et al. | |
| 7,342,214 B2 | 3/2008 | Tuschel et al. | |
| 7,400,405 B2 | 7/2008 | Sadeghi et al. | |
| 7,416,902 B2 | 8/2008 | Pletcher et al. | |
| 7,511,809 B2 | 3/2009 | Schneider et al. | |
| 2002/0031843 A1 | 3/2002 | Harmon | |
| 2003/0223063 A1 | 12/2003 | Hill et al. | |
| 2004/0043443 A1* | 3/2004 | Lejeune | 435/29 |
| 2004/0155202 A1* | 8/2004 | Poteet et al. | 250/461.1 |
| 2005/0105079 A1 | 5/2005 | Pletcher et al. | |
| 2005/0179893 A1 | 8/2005 | Hill | |
| 2005/0206892 A1 | 9/2005 | Wang et al. | |
| 2005/0214168 A1 | 9/2005 | Lin et al. | |
| 2005/0229698 A1 | 10/2005 | Beecroft et al. | |
| 2005/0280814 A1 | 12/2005 | Iuliano | |
| 2006/0061762 A1 | 3/2006 | Dwight et al. | |
| 2007/0273610 A1 | 11/2007 | Baillot | |

FOREIGN PATENT DOCUMENTS

FR     2571144 A1     4/1986

OTHER PUBLICATIONS

Higdon N S et al.," Laser Interrogation of Surface Agents (LISA) for Chemical Agent Reconnaissance," Proceedings of the SPIE- The International Society for Optical Engineering SPIE-Int., vol. 4722, 2002, pp. 50-59.

Ponsardin P L et al., "Expanding Applications for Surface-Contaminant Sensing Using the Laser Interrogation of Surface Agents (LISA) Technique," Proceedings of the SPIE- The International Society for Optical Engineering SPIE-Int., vol. 5268, No. 1, 2003, pp. 321-327.

Sedlacek A J III et al., "Application of UV-Raman Spectroscopy to the Detection of Chemical and Biological Threats," Proceedings of the SPIE- The International Society for Optical Engineering SPIE-Int., vol. 5269, No. 1, 2003, pp. 23-33.

Search Report in counterpart European Application No. 07868185.5, dated Apr. 26, 2010.

* cited by examiner

METHOD, APPARATUS AND SYSTEM FOR RAPID AND SENSITIVE STANDOFF DETECTION OF SURFACE CONTAMINANTS

RELATED APPLICATION

This application claims priority to U.S. Provisional Application No. 60/784,465, filed Mar. 22, 2006, the entirety of which is incorporated herein by reference.

GOVERNMENT RIGHTS

This invention was made under U.S. Government Contract No. DAAD13-03-D-0018. The U.S. Government may have certain rights in the invention.

BACKGROUND OF THE INVENTION

The present invention relates to applied ultraviolet (UV) Raman spectroscopy and chemical detection and identification. More specifically, the present invention relates to devices, systems and methods for remotely detecting hazardous substances that may be on a surface.

In the field of chemical sensing or detecting, it is desirable to quickly detect substances at a contaminated scene and report information about the substances types and locations in order to prevent others from coming into contact or influence with the detected substance. It is also a key factor in improving consequence management by providing the decision makers with the information needed to scale and direct the response effort.

Spectroscopy techniques are used to analyze substances and techniques have been developed for the non-destructive testing of surface-deposited substances in solid and liquid phases. Such techniques include Fourier Transform Infrared Spectroscopy (FTIR), X-ray fluorescence, gas chromatography and mass spectrometry (GC-MS), and Infrared Raman spectroscopy (IR Raman). Currently available surface-hazard detectors are "point-and-shoot" devices, in which the device operator holds a sensing probe on a specific location at very close range and dwells on that specific location for an amount of time to provide sufficient integration time in the detector or, in the case of GC-MS, to intake enough surface compounds in vapor phase to carry out the analysis. Thus, these devices require the operator to approach very close to a potentially harmful substance and maintain proximity to that substance long enough to obtain a single measurement. The task of surveying a large area or region for potentially harmful substances is therefore daunting and requires judicious sampling strategies to maximize the efficiency of the process. The most challenging aspect associated with searching contaminants dispersed on a surface resides in the variety of chemical species a sensor is exposed to during a search.

Surface contamination can be the result of an accident or intentional dispersion of the contaminant, and therefore the surface contamination can consist of a single chemical or multiple chemicals in bulk form or dispersed over a wide area. In the case of persistent patches of contamination composed of thin layers, small droplets or small particles, none of the above mentioned methods provide adequate detection capabilities.

For example, a commercially available FTIR system for emergency response requires 20 seconds to carry out a single sample-identification analysis, while the sample needs to be physically removed from the surface and presented to the sensor. Another example is a commercially available IR-Raman system for emergency response that requires a maximum distance of 15 mm and measurement times typically between 1 and 5 seconds with up to 20 seconds for some samples.

UV Raman spectroscopy has many unique properties that can be advantageously employed in the rapid standoff detection and identification of surface-deposited hazards. The high degree of information content inherent in Raman spectroscopy provides the ability to differentiate structurally similar chemicals with low false alarm rates. The information content is associated with the vibrational degrees of freedom associated with any molecule. This wealth of vibrational modes manifests itself in rich, narrow Raman peaks that provide a spectral fingerprint for a given Raman active material. Spontaneous Raman scattering, however, has an intrinsically weak cross-section. The intensity and quality of the Raman spectrum depends on (1) the wavelength, linewidth and spectral purity of the excitation light, (2) the extent to which the excitation or scattered light is absorbed, the amount of interfering fluorescence that is emitted, and the potential existence of interfering laser-induced breakdown emission of surface materials, (3) the thermal and photochemical stability of the sample under excitation, and (4) the number or chemicals simultaneously interrogated (spectral congestion). Therefore to maximize usability in practical applications, UV Raman sensors capitalize on a short wavelength resulting in larger scattering cross-sections, a reduced natural fluorescence background (no photo-bleaching required), a solar-blind spectral region below 300 nm (important for a standoff sensor) and resonance enhancement of the Raman scattering cross-section for some vibrational transitions. In addition, UV light sources below 300-nm present virtually no eye hazard to personnel wearing standard plastic or non-crystalline glass eye-protection.

A surface-hazard detection system is needed that can safely interrogate surfaces from greater distances and that can do it with a high degree of flexibility in the adjustment of the sensor field of interest. This standoff surface-hazard detection system needs also to rapidly analyze returned optical radiation from the substance in order to provide the high data throughput that enables large perimeter searches. UV Raman spectroscopy provides the foundation for this high performance sensor.

SUMMARY OF THE INVENTION

The present invention is directed to systems and methods for fast and sensitive standoff surface-hazard detection with high data throughput, high spatial resolution and high degree of pointing flexibility.

According to one embodiment of the invention, the system comprises a first hand-held unit that directs an excitation beam onto a surface that is located a distance away from the first unit and an optical subsystem that captures scattered radiation from the surface as a result of the beam of light. The first unit is connected via a link that includes a bundle of optical fibers, to a second unit, called the processing unit. The processing unit comprises a fiber-coupled spectrograph to convert scattered radiation to spectral data, and a processor that analyzes the collected signal and detect the hazardous substance. The second unit may be contained within a body-wearable housing or apparatus so that the first unit and second unit together form a man-portable detection assembly. Adjustable focus collection optics collect the Raman scattered radiation from safer distances, such as more than 0.25 m. To assist in achieving the desired focal distance from the surface to be interrogated, a visible light spot may be projected onto the surface to indicate the optimum standoff range and to indicate the location of the collection field of view.

The system of the present invention uses a UV-transmitting fiber bundle to efficiently couple the collected scattered radiation image to the spectrograph. A round multi-fiber bundle is positioned at the focal plane of telescope and fibers of the bundle are rearranged to form a single row that is used as the entrance slit of the spectrograph. The spectrograph images the entrance slit onto a pixelated light detector after the light is spatially dispersed by a grating.

The system and method of the present invention uses the pixelated light detector located at the output of the spectrograph to detect the Raman return. Several Raman returns can be accumulated in order to improve the signal to noise ratio (SNR) of a given measurement frame. A configurable number of returns are accumulated onto the detector to provide a single measurement frame, and each vertical column of pixels of the detector is binned to further improve the SNR. The resulting array of digital values extracted from the detector contains the Raman signature used by the processing unit to make a substance detection and identification. To accommodate various modes of operation of the sensor, the number of Raman returns accumulated in each measurement frame is variable. For example, during rapid search, a surface is quickly scanned and fast frame rates (i.e. less Raman-returns accumulations per frame) are important to maintain high probability of detection. Despite the associated reduction in SNR for each frame, the probability of detection is improved since each frame is composed of short total exposures ensuring a higher probability of grabbing a high-purity Raman signature (low spectral congestion) from a target compound that is being encountered during scan. The short-exposure frames allow the sensor to cope with the quick sequence made of a large variety of surface substances presented to the sensor resulting from the rapid surface-scan. In contrast, during a confirmation or identification mode, the sensor stares at the interrogated surface so that Raman signature have higher purity since less variety is presented to the sensor) and slower frame rates (more Raman-returns accumulations per frame) are important to provide high identification specificity by improving the Raman signature SNR.

The system and method of the present invention may use a continuous scan of the surface to detect contamination patches. In contrast to the point-and-shoot sensor, this sensor system of the present invention allows for rapid surface scans that range from static to up to tens of centimeters per second depending on the scenario. This is possible since the sensor can output good quality Raman measurement frames at a 10 to 25 Hz rate while maintaining a practical standoff range (i.e., 1 m). The capability to generate these high frame rates allows for capturing of Raman data in the form of "Raman-video" signal. As discussed previously, several modes of operation are possible. A search mode is used to provide maximum scan speed while screening a large perimeter. The high data throughput associated with the search mode is compatible with adaptive sampling techniques that use the real-time results to direct and optimize a search and scanning strategy.

The detection and identification system of the present invention employ a distributed architecture to maximize system-level performance. For man-portable applications it can be advantageous to separate the system into various units. One unit may be a battery-operated backpack or suitcase unit housing a scaled down version of beam directing, scattering collection and spectrum analysis into an agile configuration. A second unit, called a base station, contains processing capability for more intensive analysis of the collected spectra. Consequently, the battery-operated unit can be made lighter by carrying a small processing device that can execute a less computationally-intensive spectrum analysis algorithm.

In still another embodiment, a plurality of surface scanning sensors may be deployed to scale a search effort in large areas or regions, or buildings. All of the sensors report detection events to a centralized scene-control unit that can coordinate the search effort.

DETAILED DESCRIPTION

Figure 1:
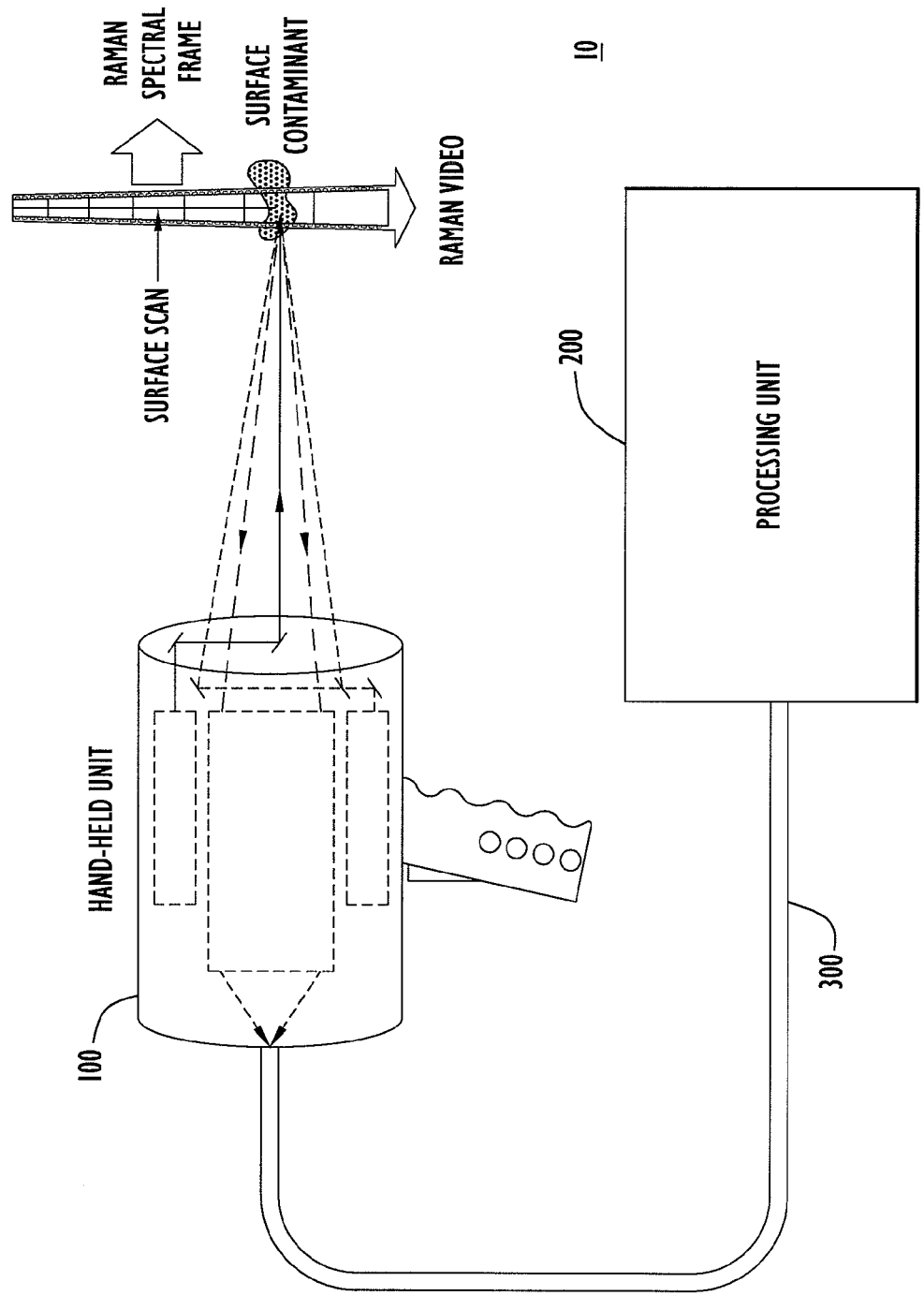
FIG. 1 is a graphical diagram of a standoff surface-hazard detection system according to one embodiment of the present invention.
Figure 2:
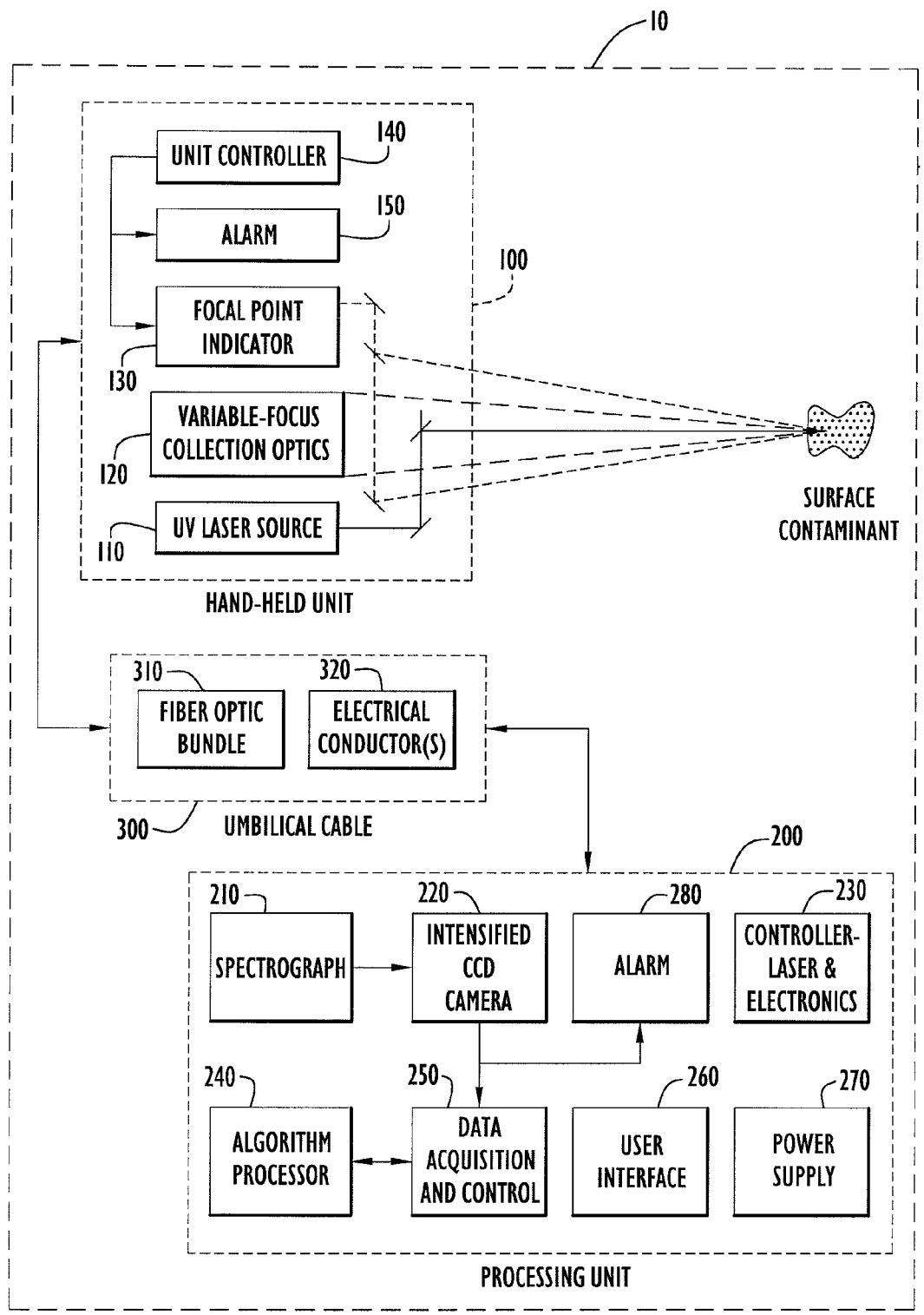
FIG. 2 is a block diagram of a standoff surface-hazard detection system according to one embodiment of the invention.

Referring first to FIGS. 1 and 2, a standoff hazard detection system 10 according to an embodiment of the invention is described. The detection system 10 comprises a hand-held unit 100 and a processing unit 200. The hand-held unit 100 is also referred to herein as a first unit or a "wand" unit or device and the processing unit 200 is also referred to herein as a second unit or a data acquisition/processing unit. The hand-held unit 100 is connected by an umbilical cable 300 to the processing unit 200. As used herein, the term "standoff" in connection with a standoff hazard detection and identification system means a distance or range of more than 0.25 meters between the detecting apparatus and the surface that is being interrogated and on which a hazardous substance or contaminant may reside.

The system 10 achieves fast and sensitive standoff surface-hazard detection with high data throughput, high spatial resolution and high degree of pointing flexibility. This distinctive mode of operation enables new, efficient, surface-contamination search strategies. In contrast to the existing "point-and-shoot" techniques, the system 10 enables acquiring single-pixel "Raman-video" footages of a contaminated scene as depicted in FIG. 1.

The hand-held unit 100 is held in the hand of a user and is used to direct a light beam onto a surface to analyze with spectroscopy techniques a substance in solid or liquid phase on the surface in order to determine a composition of the substance. The substance may be a hazardous substance or contaminant, such as a chemical, biological or explosive substance on the ground, floor, wall or other objects, and the substance may be present in bulk or sparsely dispersed over a surface. Thus, as described in further detail hereinafter, the system 10 may be designed for use by one person or by a two-person team. The operators may be wearing hazard-protective gear. Generally, the hand-held unit 100 is used to interrogate a suspected surface at a stand-off distance of approximately 0.5 to 3 meters, and to return spectrum related data about the threat to the processing unit 200 that analyzes the spectrum related data in direct line of sight, determines whether there is a presence of a harmful threat, and rapidly issues a notification of the type of threat, e.g., in less than or equal to 100 ms. The processing unit 200 may further comprise a display device, such as a touch screen display or a wearable heads-up display, as one type of a user interface with the system 10. The display device may provide a visual (and optionally an audio) notification with textual explanation of the details associated with the detected hazardous substance. The display screen may be a type that is suitably compatible for use by a person wearing an environmental suit.

Elements of the system 10 are described in more detail in connection with the block diagram of FIG. 2. The hand-held unit 100 comprises a laser light source 110, variable-focus collection optics 120, a focal point indicator 130, an alarm 150 and a controller 140. The laser light source 110 emits an interrogating light beam and the collection optics 120 capture the returned optical energy and directs that energy over the umbilical 300 to a spectrograph 210 in the processing unit 200. The focal point indicator 130 is described hereinafter.

The laser source 110 in the hand-held unit generates an interrogating light beam directed at a surface of interest. The collection optics 120 capture returned optical energy from the surface of interest. The light beam may any suitable type of light that is useful for analyzing characteristics of a liquid and/or solid substance on a surface. For example, the laser source 110 may produce a beam of light in the ultraviolet (UV) spectrum, such as an Nd:YAG or Nd:YLF laser. Further, the laser source 110 may produce UV light that is substantially monochromatic (a single wavelength or is limited to a narrow range of wavelengths). Moreover, the laser source 110 may produce Raman light such that the returned optical energy consists of Raman scattered optical energy that is analyzed using spectroscopy techniques.

The cable 300 comprises a fiber optic bundle 310 to couple the optical energy captured by the hand-held device 100 to the processing unit 100. The cable 300 also comprises at least one electrical conductor 320 (and more likely a plurality of electrical conductors) used to communicate commands from the processing unit 200 to the hand-held unit 100 and other data from the hand-held unit 100 to the processing unit 200.

The processing unit 200 may take on a variety of forms. FIG. 2 shows that the processing unit 200 comprises a spectrograph 210, an intensified charge-coupled device camera (ICCD) 220 that serves as a pixilated detector, a controller 230 for the laser and associated electronics, an algorithm processor 240, a data acquisition and control processor 250, a user interface 260 (comprising a display screen), and a power supply 270. As is known in the art, the spectrograph comprises a diffraction grating to disperse the scattered radiation onto the ICCD 220. The ICCD 220 may be integrated into the spectrograph 210. The power supply 270 may be a rechargeable battery capable of storing a sufficient amount of charge to enable relatively long usage intervals in the field before requiring a recharge. Alternatively, or in addition, the power supply 270 may be capable of receiving power from a standard power outlet. The algorithm processor 240 may be a computer containing memory in which one or more programs are stored that cause the computer to perform various spectroscopy analysis algorithms and control procedures. The processor 240 may compare the spectral data with spectral data for a plurality of known substances in order to determine whether the spectral data is that of a known or foreign substance. There is also an alarm device 280 that, when activated by an alarm trigger signal, produces an audible and/or visual alert notification. The alarm device 280 may be integrated into the user interface 260.

The data acquisition and control processor 250 located in the processing unit 200 provides overall system control, including management of inputs and outputs via the user interface 260 as well as control signals to and from the hand-held unit 100. The algorithm processor 240 executes the algorithms that analyze the output of the spectrograph 210 to determine whether the returned optical energy (e.g., Raman spectrum) resulted from interaction of the UV laser light with a hazardous substance. The algorithm processor 240 comprises a memory that stores a database or library of signatures that are used in the spectroscopy analysis it performs on the Raman spectral data.

The light beam directed at the surface to be scanned may comprise discrete pulses of UV light to create the Raman signal from the surface sample. In another embodiment, the laser source 110 may be a continuous wave (CW) UV light source. Raman signal strength can be maximized by conditioning the excitation beam characteristics. Locating the light generator portion of the light source 110 in the hand-held unit 100 allows for properly shaping the transmitted excitation beam and to maximize the amount of delivered energy. However, the light source 110 in the hand-held unit 100 may be the final UV-conversion stage that is pumped by a laser that actually resides in the processing unit 200 and coupled to the UV-conversion stage through an optical fiber in the umbilical cable 300.

A high quality UV excitation beam is important because it allows for tightly focusing the excitation beam onto the interrogated surface. A tight laser focus (e.g. less than one millimeter in diameter) over the entire standoff range of the system is useful for several reasons. First, the excitation spot diameter constitutes the imaging object of the collection optics. Since the collection optics 120 in the hand-held unit 100 uses a high numerical aperture to collect as much radiation as possible, the small size of the excitation spot makes it possible to efficiently couple that image into the rest of the optical receiver chain. A second reason to constrain the excitation spot to a small diameter is the desire to limit the total number of chemical species being interrogated simultaneously. The collected total Raman signature results from the superposition of the individual Raman signatures associated with each chemical being excited. A large excitation spot may provide a larger number of Raman signatures since there is a higher probability to encounter more chemical species, resulting in a less distinct—more spectrally congested—total Raman signature. By interrogating a single chemical specie at a time using a tightly focused beam, high-purity Raman signatures can be generated. A third reason to constrain the excitation spot to a small diameter resides in the quantity of signal associated with each Raman signature that is generated. A small excitation spot provides efficient delivery of most of the available excitation photons to the target of interest, in the case when the target is a small droplet or particle. This allows the Raman signature of the target chemical to dominate the total Raman signature and to scale that signature above the sensor noise floor, hence improving the limit of detection of the sensor. Finally, another reason to constrain the excitation spot to a small diameter is to provide an accurate geo-location of the contaminant since direct correlation between detection event and location of interrogating beam can be made. In summary, this small interrogation spot constitutes the notion of "single-pixel" Raman signature that is fundamental to the "Raman-video" sensor concept described hereinafter.

The variable-focus collection optics 120 allow for the collection of the Raman scattered radiation from safer distances. i.e., "standoff" distances. While the adjustment of the standoff distance is not required, the measurement process is enhanced by providing this adjustability since the sensor has a limited depth of field for a given standoff range. One way to adjust the focus distance is to adjust the separation distance between optical elements that form the variable-focus collection optics 120. Another way to adjust the focus distance is to adjust the separation between a most distal telescope optical element and the input of the fiber bundle 310 coupling the optics to the spectrograph 210. In all cases only a single component needs to be translated to adjust the sensor standoff range. The optical element can be translated by the operator on demand using a manually actuated mechanism, using a motorized mechanism or a hybrid mechanism. In one embodiment, focus adjustability from 0.5 to 3 m is provided by translating the primary mirror. In another embodiment, the collection optics have a fixed focus at 1 m to simplify the mechanical design. Examples of the variable-focus collection optics 120 are described in more detail hereinafter in connection with FIGS. 4A-4D. In addition, an auto-focus system may be employed to automatically move one of the optical elements in the collection optics 120 based on knowledge gained from the focal point indicator 130, described in more detail hereinafter.

The focal point indicator 130 generates a visible light spot projected onto the interrogated surface to indicate the optimum standoff range and to indicate the location of the collection field of view. Once the collection optics 120 is adjusted to the desired focus distance, this visible spot acts as the target designator as well as the indicator to maintain correct standoff distance. This feature adds to the pointing flexibility associated with the hand-held unit 100 and enables efficient surface scans. One way to accomplish this is by intersecting two laser diode pointers at the optimum standoff distance. Maintaining minimum separation between the two or more projected spots ensures proper focusing of the collection optics. Pointing the diode lasers through the telescope optics allows accurate indication of the standoff range for all adjustments of the telescope focus distance. Alternatively, a fiber coupled visible light can be used. The fiber output can be projected through the telescope to image the collection field of view onto the interrogation surface. In this case, a dichroic mirror is used to separate the UV Raman receive channel from the visible designator channel. Examples of the focal point indicator 130 are described hereinafter in connection with FIGS. 4A-4D. Again, as mentioned above, an auto-focus system may be employed to interpret the distance to the surface based on the light spot projected by the focal point indicator 130 to automatically adjust the variable collections-optics 120.

In accordance with another embodiment of the present invention that is described hereinafter in conjunction with FIG. 3, a distributed architecture is employed to maximize system-level performance. While the embodiment shown in FIG. 2 locates in the processing unit 200 several of the major functions (i.e., search and identification modes) in a single package, for man-portable applications it can be advantageous to further separate the processing functions across multiple units. For example, a battery-operated backpack or suitcase unit may be provided to house a scaled down version of the sensor component (hand-held unit 100 and processing unit 200) to enable the collection of the scattered signatures in an agile configuration. A base station or stationary unit is also provided that provides docking functions, enabling the battery-operated unit to be charged, turned on and brought to a steady state while being powered by the base station. The base station can also house the calibration equipment as well as an additional processing unit that is more powerful than that in the first unit. In this case, the battery-operated unit can be made lighter by carrying a smaller processor that provides a lower fidelity search-mode function using a less computationally-intensive spectroscopy analysis algorithm. This onboard capability, while providing higher false alarms, enables the search mode and gives the user an always-present capability while in a hostile environment. The battery operated unit can in parallel transmit the Raman frames to the base station that runs a more computationally-intensive (higher fidelity) algorithm associated with the identification mode to more precisely identify a hazard.

According to this embodiment of the invention, the equipment for standoff interrogation of a suspected hazardous substance may be configured in a man-portable or wearable assembly 600 comprising a hand-held unit 700 and a body-wearable unit 800. This configuration is described with reference to the block diagram of FIG. 3. The hand-held unit 700 comprises a laser 710, collection (telescope) optics 720, a controller 730 and an alarm device 740, similar to those components shown in FIG. 2 and described above. The umbilical cable comprises a fiber optic bundle 910 and an electrical conductor bundle 920 similar to the cable 300 shown in FIG. 2. The wearable unit 800 is connected to the hand-held unit 700 via the umbilical cable 900 and comprises the spectrograph 810, an ICCD 815, a control and data acquisition processor 820, a display 830, a power supply 840 (e.g., battery pack), a radio frequency (RF) wireless transceiver/modem 850 for supporting wireless communication with a base station 1000($i$) via an antenna 805 and an alarm device 860. The power supply 840 supplies power for the components in the wearable unit 800 as well as for components in the hand-held unit 700. The display 830 may be a snap-on or flip-down display mechanism viewable by the operator, or a display visible on a visor, such as a heads-up display. The display 830 can be used to display information to the user concerning the detection of hazardous substances. In many respects, the wearable unit 800 is similar to the processing unit 100 in the first embodiment and the hand-held unit 700 is similar to the hand-held unit 200 in the first embodiment.

The man-portable assembly 600 may communicate with one or more base stations 1000(1) to 1000(N). A base station comprises an antenna 1005, an RF wireless transceiver/modem 1010, an analysis processor 1020, a display 1030 for the base station operator, and a facility power supply 1040. The base station 1000($i$) may be mounted or used in a vehicle and driven by a power system of the vehicle, as an example. Alternatively, the base station may be at a fixed position. Furthermore, the base station 1000($i$) may be man-portable in the sense that it can be contained in a wearable apparatus or may be embodied as a laptop computer equipped with suitable wireless communication capabilities. The base station 1000($i$) may further comprise or have integrated therein an alarm device similar to those included in the man-portable assembly 600. The base station 1000($i$) may have a docking port or unit 1050 that is capable of connecting to the man-portable assembly 600 by way of a suitable connection cable to charge the power supply 840, activate the assembly 600 and bring it to a steady state through the facility power 1040 of the base station. As mentioned above, the processor 1020 may also interact with the relevant components in the manportable assembly 600 in order to calibrate the spectrograph 810 in the wearable unit 800. The docking unit 1050 may include a battery charger that, when the wearable unit 800 is docked, charges the power supply 840.

There are several possible operational scenarios between a base station 1000(i) and the man-portable assembly 600. In one scenario, the processor 820 in the wearable unit 800 converts the output of the spectrograph 810 into digital spectrum data signals, optionally compresses the spectrum data and transmits this spectrum data via the RF transceiver 850 to one or more of the base stations 1000(1) to 1000(N). The analysis processor 1020 in a base station 1000(i) receives the spectrum data from the wearable unit 800 and performs the analysis of the spectrum data to detect and identify a hazardous substance and displays the results of its computations on the display 1030. After performing its analysis, the base station 1000(i) may transmit a signal back to the wearable unit 800 that indicates the nature/identity of a detected substance. For example, if a harmful substance is detected, the transmitted signal may trigger an audible and/or visual alert on the wearable unit 800 and/or the hand-held unit 700 so that the user takes suitable precautions in continuing further, or leaves the area immediately.

Optionally, the processor 820 in the wearable unit 800 may perform a faster, but lower-fidelity analysis, of the spectrum data produced by the spectrograph 810 in order to alert the user in real-time or near real-time of detection of a hazardous substance, but potentially with a lower confidence. This is the so-called search mode referred to above. The wearable unit 800 will also transmit the spectrum data to a base station 1000(i) that performs a higher fidelity, higher-confidence, analysis but which may take some additional time. This is the so-called identification mode referred to above, and it uses a more complete library of signatures. This processing allocation scheme permits more advanced search strategies, as described below in greater detail in connection with FIGS. 7 and 8.

Figure 3:
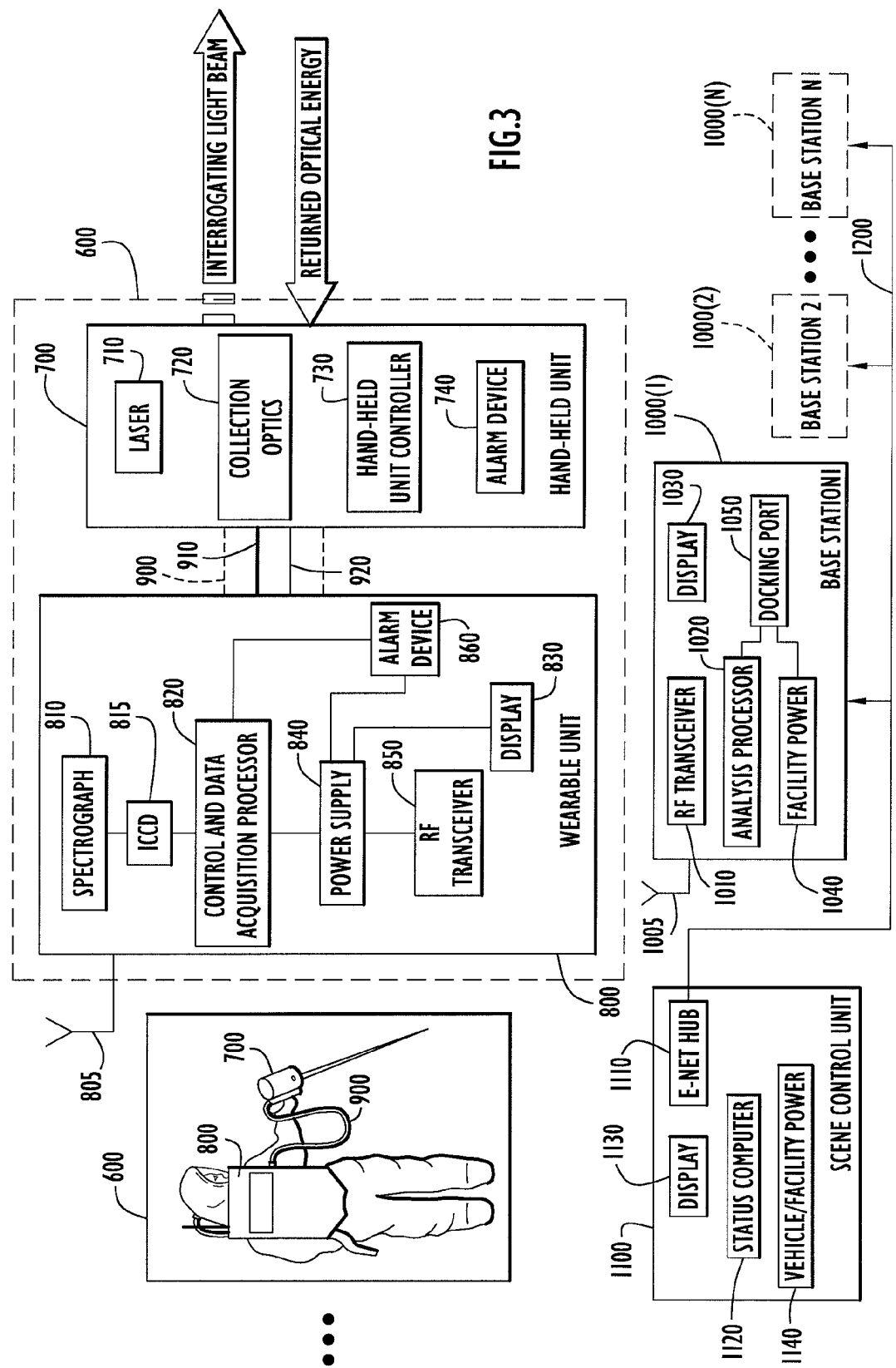
FIG. 3 is a block diagram of a standoff surface-hazard detection system according to an embodiment of the invention.

One advantage of separating the detection processing from the data collection as depicted by the configuration of FIG. 3 is that the collected data can be transmitted to multiple base stations (simultaneously or sequentially) and each base station can make its own analysis and be alerted by the man-portable assembly 600 that a hazardous substance has been detected. If a plurality of man-portable assemblies is deployed, each assembly would have a unique identifier that is used when transmitting data to a base station so that a base station can distinguish between man-portable assemblies. Thus, the information about a hazardous substance can be rapidly and widely distributed.

In yet another embodiment of the present invention, a suite of surface scanning man-portable assemblies 600 are provided to scale the search effort in large perimeters or buildings. In this case all manportable assemblies 600 report detection events to a centralized scene-control unit that can coordinate the search effort. Adaptive sampling at the scene level is possible with this multi-sensor configuration. To this end, one or more of the base stations 1000(1) to 1000(N) may be linked to a further remotely located master scene control unit 1100 that coordinates several base stations/man-portable assemblies. The scene control unit 1100 may include a network interface, such as an Ethernet hub (E-Net hub) 1110, a status computer 1120, a display 1130 and a power supply 1140. Each of the base stations 1000(1)-1000(N) would also have an Ethernet interface component to facility communication over the network 1200. The scene control unit 1110 may be operated by a commander on the scene, for example, whose responsibility it is to coordinate activity with respect to actual or potential detection of a hazardous substance.

Turning to FIGS. 4A-4D, embodiments of the hand-held unit 100 are described in more detail. In one embodiment shown in FIG. 4A, the hand-held unit 100 may comprise a main housing 102 and a hand-grip portion 104. The housing contains the collection optics 120 and also serves as a support for the laser 110. The laser 110 is mounted on the bottom of the housing 102. Fold mirrors 112 and focusing optical elements 114 direct the laser beam to be emitted co-linearly with the bore sight of the collection optics 120. There is a laser power meter 116 that receives a small fraction of the laser light via one of the fold mirrors 112 to permit monitoring of the laser beam being transmitted. The fold mirrors 112 can tip or tilt to adjust the optical path of the laser beam. The housing 102 has a front window 108 sized to support the optical elements associated with the laser 110 and the collection optics (telescope) 120 thereby eliminating the need for spider supports that would otherwise interfere with detection of Raman backscatter. The collection optics 120 comprises a primary mirror 122 and a secondary mirror 124. In this embodiment, the primary mirror 122 is fixed and the secondary mirror 124 is movable along an optical axis or bore sight of the device. The secondary mirror 124 can also tip and tilt to adjust the optical path for the returned optical energy through the telescope 120. The collection optics 120 focuses any reflected backscattered (e.g., UV Raman) radiation into the fiber optic bundle 310 that is connected to the hand-held unit 100 and that in turn delivers the returned scattered radiation to the spectrograph 210 contained in the processing unit 200 (FIG. 2).

Figure 4A:
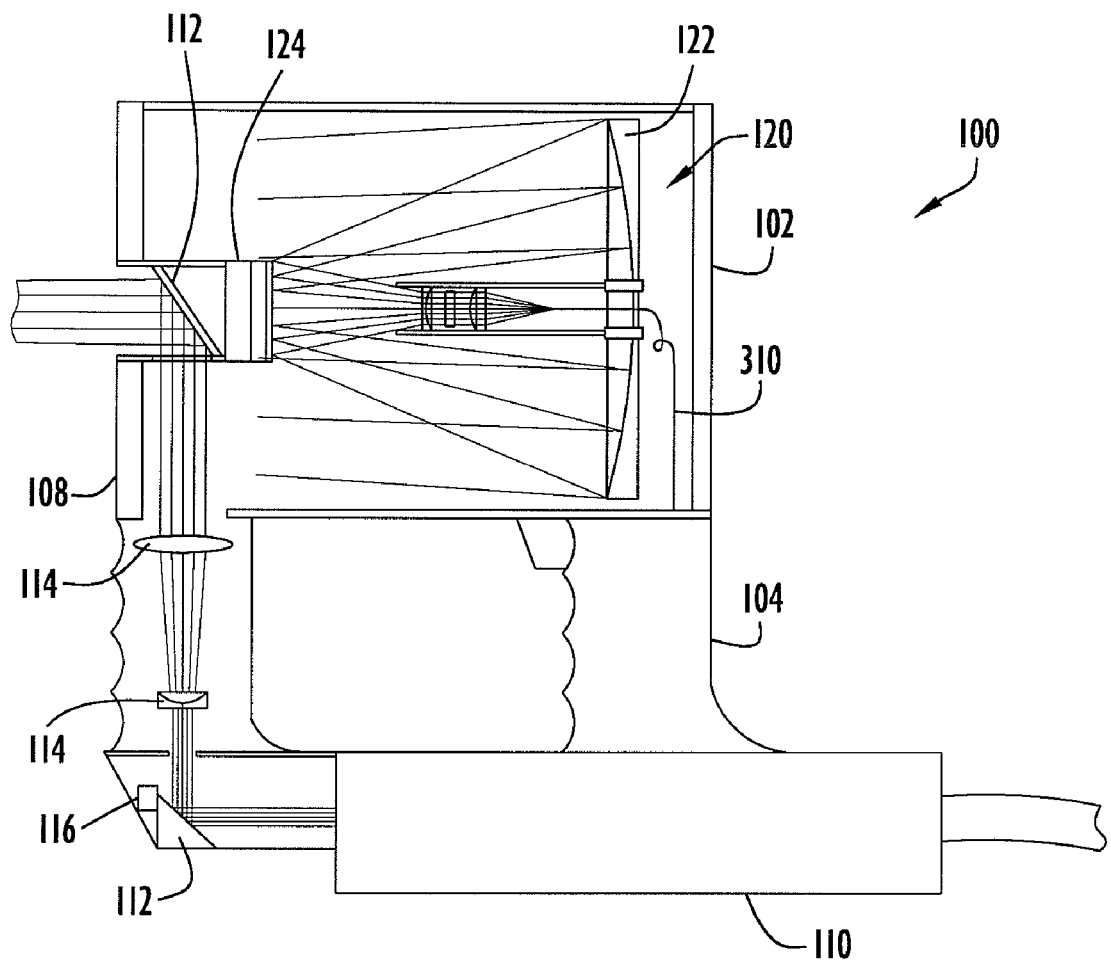
FIGS. 4A, 4B, 4C and 4D illustrate several configurations of a hand-held device forming a part of the standoff surface-hazard detection system according to embodiments of the invention.
Figure 4B:
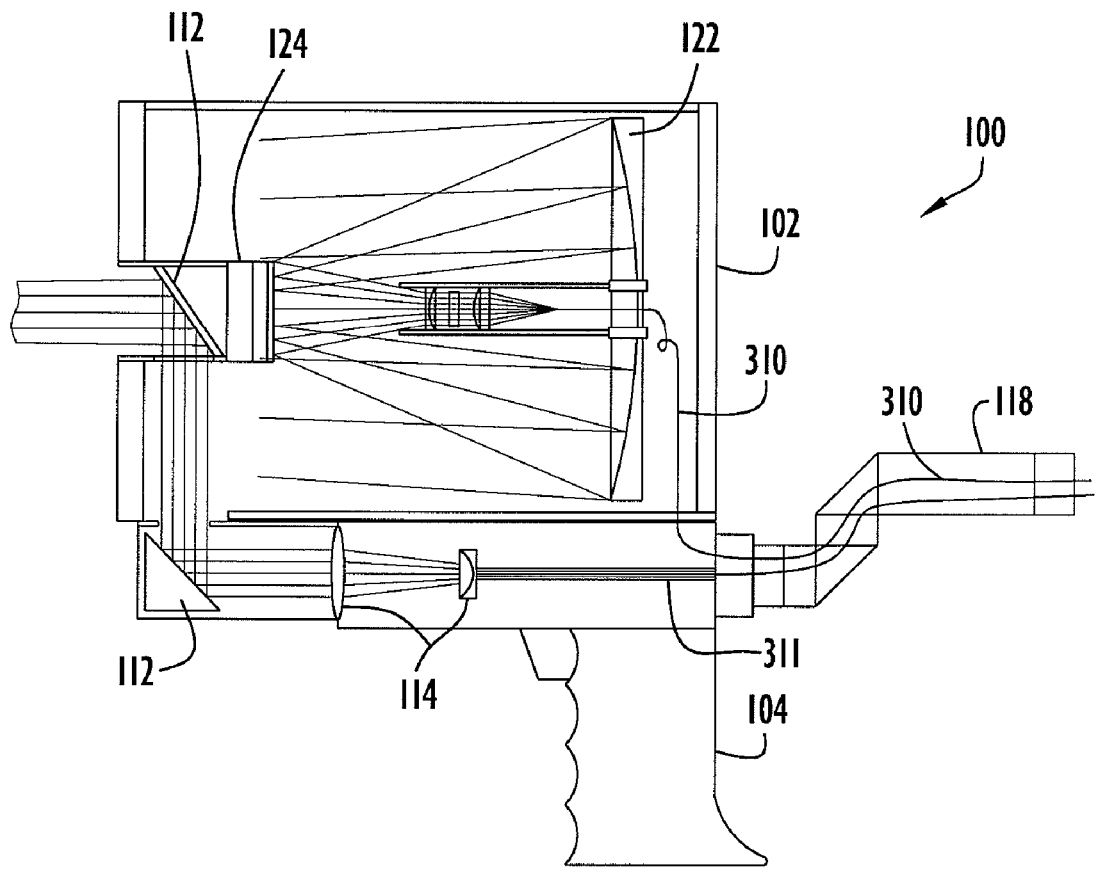

In another embodiment of the hand-held unit 100 shown in FIG. 4B, there is an articulated arm connection 118 connected to a base of the housing 102 that can tip and tilt the optical axis of the laser beam. This allows the laser source to be located in the processing unit 200 instead of in the hand-held unit 100. There is an optical fiber 311 that supplies the laser beam from the UV source in the processing unit 200 to the focusing optic elements 114 in the hand-held unit 100. The other components of the hand-held unit 100 shown in FIG. 4B may have the same configuration as those shown in the embodiment of FIG. 4A.

Figure 4C:
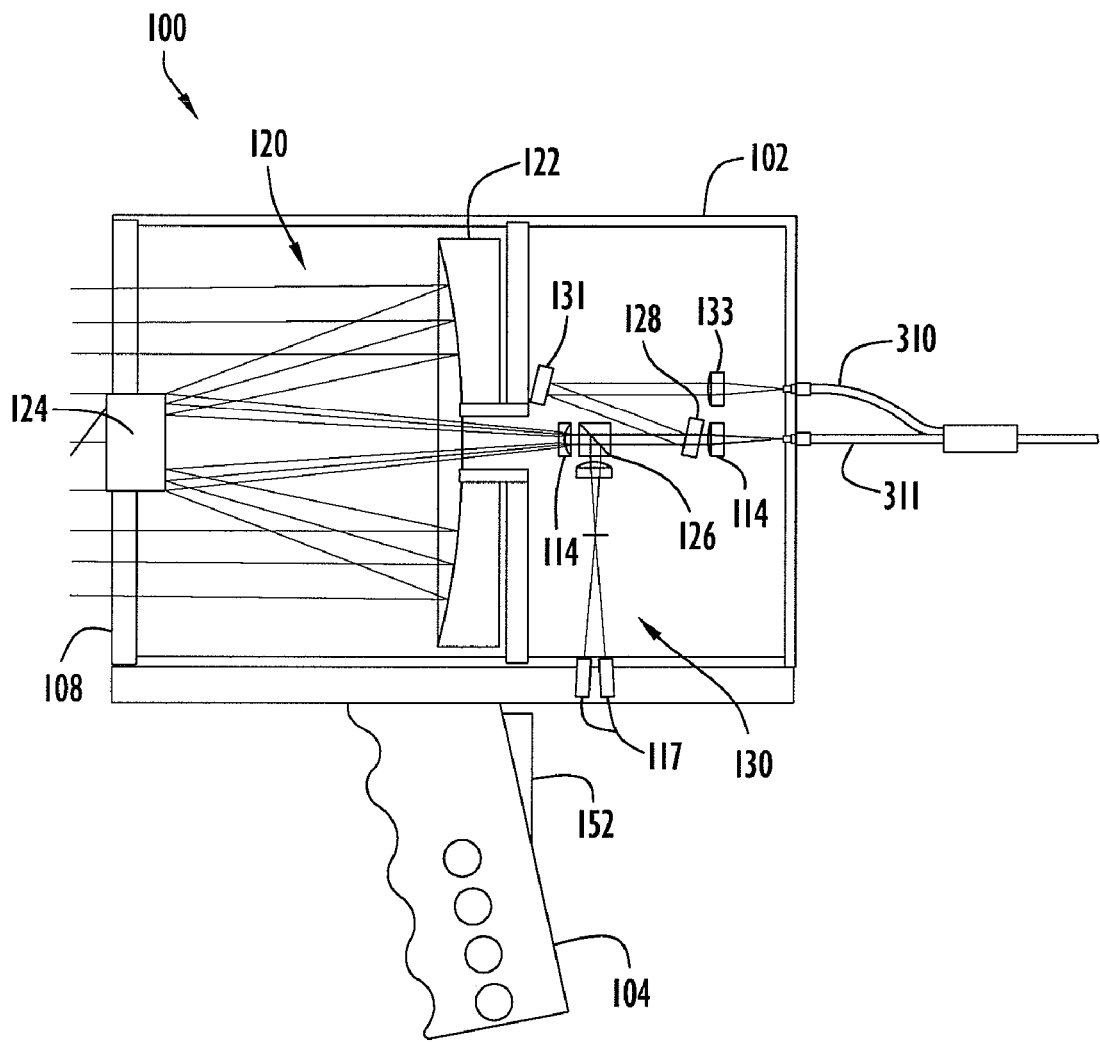

In yet another embodiment of the hand-held unit 100 shown in FIG. 4C, a transceiver configuration is used. In this case, the UV excitation light is transmitted through the collection optics 120 using the same path as the received scattered radiation. The UV laser beam is coupled through an optical fiber 311 to the focusing optical elements 114. Like the embodiment of FIG. 4B, the UV laser source resides in the processing unit 200. The collection optics 120 comprise a primary mirror 122, a secondary mirror 124, a UV Raman edge filter 128, a mirror 131 and a focusing optical element 133. In this embodiment, the primary mirror 122 is movable and the secondary mirror 124 is fixed. The UV Raman edge filter 128 separates the transmitted UV excitation beam from the returned scattered radiation. FIG. 4C also illustrates the focal point indicator 130 comprising at least two target-designator laser diodes 117 that are spaced apart from each other on the side of the housing 102 and pointed inward to direct their respective beams through a lens to a dichroic mirror 126 that reflects the light beams from the diodes into the bore sight of the hand-held unit 100 and out the window 108 to a surface for purposes of assisting in achieving the proper or desired focusing distance. FIG. 4C also shows a "dead man" switch 152 on the grip or handle 104 to disable the hand-held unit 100 when it is not in a user's hand.

Figure 4D:
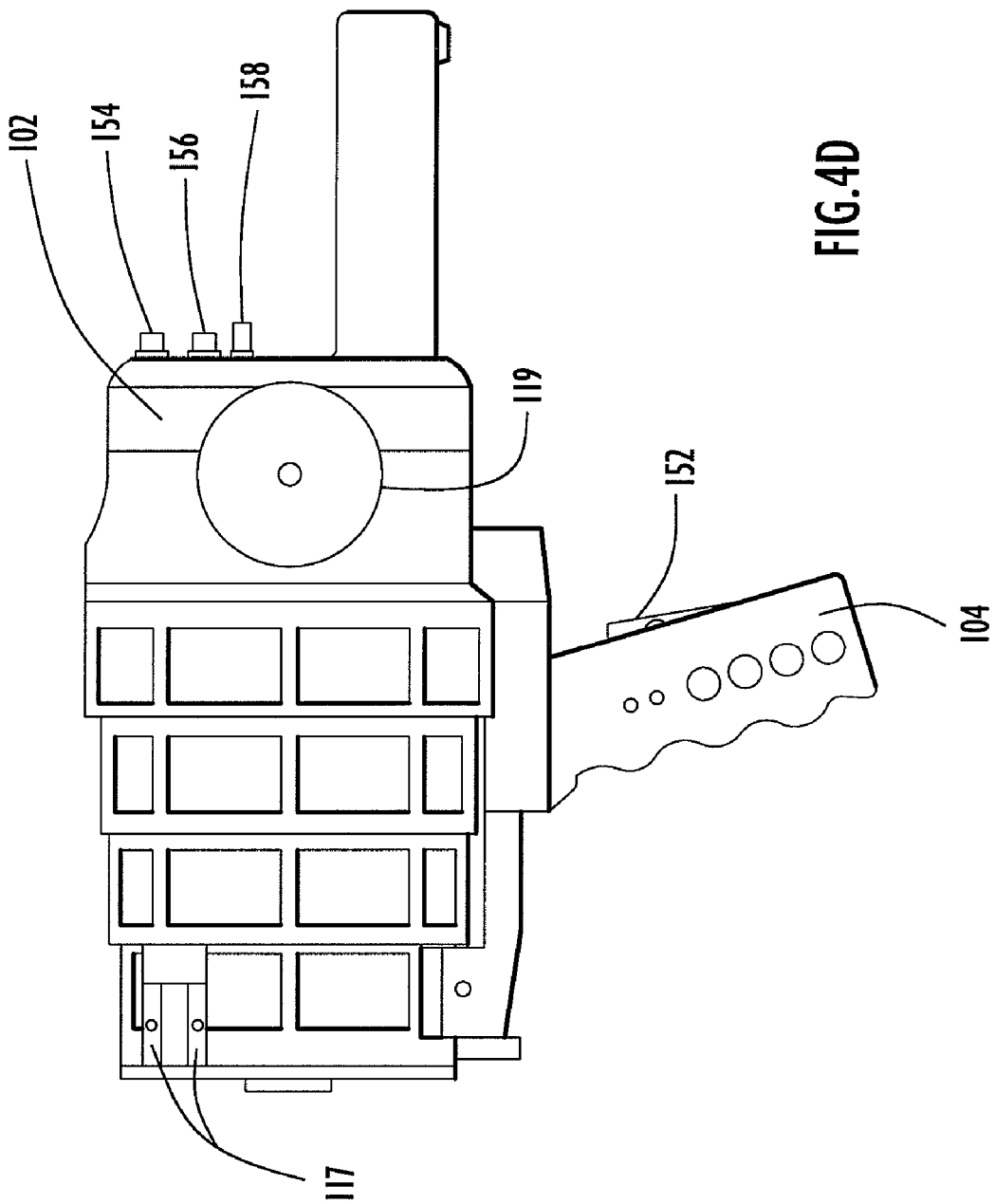

FIG. 4D shows a side view of a hand-held unit 100 according to still another embodiment. On opposite sides of the housing 102 the two focusing diodes 117 are positioned as in the previous embodiments, to assist the user to manually keep the hand-held unit 100 at the proper focal distance from the surface being interrogated. The diodes 117 are angled inward with respect to each other such that the beams they emit intersect on the surface at a focal point of the collection optics 120 a predetermined distance from the hand-held unit 100, e.g., approximately one meter. The point of intersection corresponds with the optimum focus distance of the collection optics 120. There are large focus adjustment knobs 119 on the side of the housing barrel. By turning these knobs, either the primary mirror 122 (for the embodiment of FIG. 4C) or the secondary mirror 124 (for an embodiment of FIG. 4B) is translated along the optical axis of the device and the standoff focus distance is modified accordingly. There are two switches 156 and 158 located on the back of the unit hand-held 100. To make the hand-held unit 100 operational, these three switches are actuated in order. Specifically, after a software operation at the processing unit 200 enables the system, the dead man switch 152 on the handle 104 is first compressed to close an operating circuit. Next, switch 156 on the back of the hand-held unit 100 is actuated to turn on the focusing diodes 117. Finally, the switch 158 is actuated to turn on the laser 110 or open a physical shutter on the device 100 that permits the laser light to be emitted. One or more lights (e.g., LEDs) 154 on the back of the unit 100 may be provided to indicate whether the unit is on and operational As described above, the UV-transmitting fiber bundle 310 efficiently couples the returned optical into the spectrograph 210. The fiber bundle 310 may comprise a round multi-fiber bundle that is positioned at the focal plane of collection optics 120 and at the other end of the bundle the individual fibers are rearranged to form a single row that is used as the entrance slit of the spectrograph 210. The spectrograph 210 images the entrance slit onto a pixelated light detector of the ICCD camera 220 after the light is spatially dispersed by a grating of the spectrograph 21.

The pixelated light detector of the ICCD camera 220 located at the output of the spectrograph 210 detects the Raman return energy. Several Raman returns can be accumulated in order to improve the signal to noise ratio (SNR) of a given measurement frame. Once the selected number of returns is accumulated onto the ICCD camera 220 or other pixelated detector device to provide a single measurement frame, each vertical column of pixels is binned to further improve the SNR. The resulting array of digital values extracted from the ICCD camera 220 contains the Raman signature used by the processing unit 200 to make a chemical detection and identification. Thus, the pixelated detector (e.g., ICCD 220) generates measurement frame based on one or an accumulation of a plurality of returns of scattered radiation from the surface To accommodate various modes of operation of the sensor system 10, the number of Raman returns accumulated in each measurement frame is variable. For example, during a rapid search mode, a surface is quickly scanned and fast frame rates (i.e. less Raman-returns accumulations per frame) are important to maintain high probability of detection. Despite the associated reduction in SNR for each frame, the probability of detection is improved since each frame is composed of short total exposures ensuring a higher probability of capturing a high-purity Raman signature (low spectral congestion) from a target compound that is being encountered during the scan. The short-exposure frames allow the sensor system 10 to cope with the quick sequence of a large variety of surface compositions presented to the sensor resulting from the rapid surface-scan. In contrast, during a confirmation run mode (also called identification mode), the sensor stares at the interrogated surface (i.e., Raman signature have higher purity since less variety is presented to the sensor) and slow frame rates (i.e. more Raman-returns accumulations per frame) are important to provide high identification specificity by improving the Raman signature SNR. During a confirmation run mode, saturation of the detector can occur. In this case, an auto-gain feature may be provided for each frame by stopping accumulations before reaching saturation.

The system 10 may continuously scan a surface to detect contamination patches. In contrast to the point-and-shoot sensor, this system 10 of the present invention allows for rapid surface scans that range from static to up to tens of cm-per-second depending on the scenario. This is made possible because the system 10 can generate good quality Raman frames at a 10 to 25 Hz rate in the search mode while maintaining a practical standoff range or distance (i.e., 1 m). Higher frame rates are possible but ultimately the associated reduction in SNR limits the practical frame rate. The capability to generate these high frame rates is also fundamental to the "Raman-video" sensor concept described above. In terms of a scanning rate coverage, the system of the present invention can scan a surface at a rate up to tens of centimeters per second. The high data throughput associated with the search mode is compatible with adaptive sampling techniques that use the real-time results to direct and optimize the search strategy. In this case, it may be desirable to increase the sensor probability of detection (in a lower fidelity analysis mode) at the cost of increasing the probability of false alarm. In this lower-fidelity mode false alarms have low regret consequences since they only trigger a tighter scrutiny by prompting the user to switch to the identification mode. The identification mode provides a low probability of false alarm but requires that the user stops scanning and stares at the suspected area. This lower probability of false alarm is rendered possible by conjunction of two factors: (1) as discussed previously, the staring and lower frame rates result in high-purity Raman signatures with high SNR, both improving the capability of the algorithm to perform a correct identification, and (2) the lower frame rate associated with the identification mode allows the processing unit 200 to use more computationally-intensive and sophisticated algorithms, and more extensive Raman spectra libraries to result in a positive match.

Figure 5:
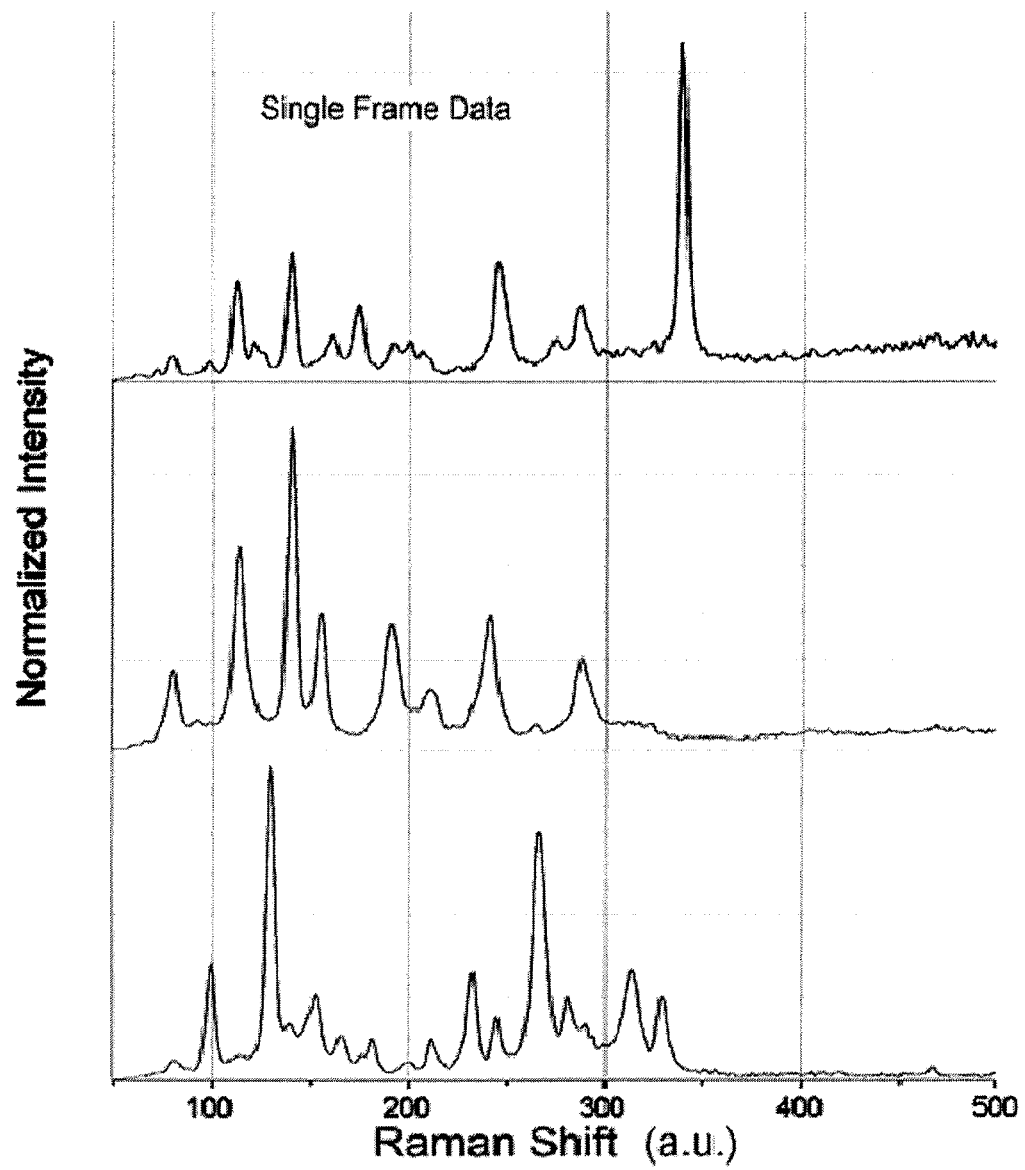
FIG. 5 illustrates plots for a single measurement frame of data derived from scanning a surface according to the embodiments of the present invention.

FIG. 5 shows example an example of Raman data for a single "frame" taken at 25 Hz repetition rate from a 1 m standoff range. This figure illustrates the quality of data achieved by the sensor configuration for purposes of enabling the "Raman video" concept described above. FIG. 5 also illustrates that the system 10 may be operated to detect and identify substances with a high data throughput in a continuous and uninterrupted manner.

Figure 6:
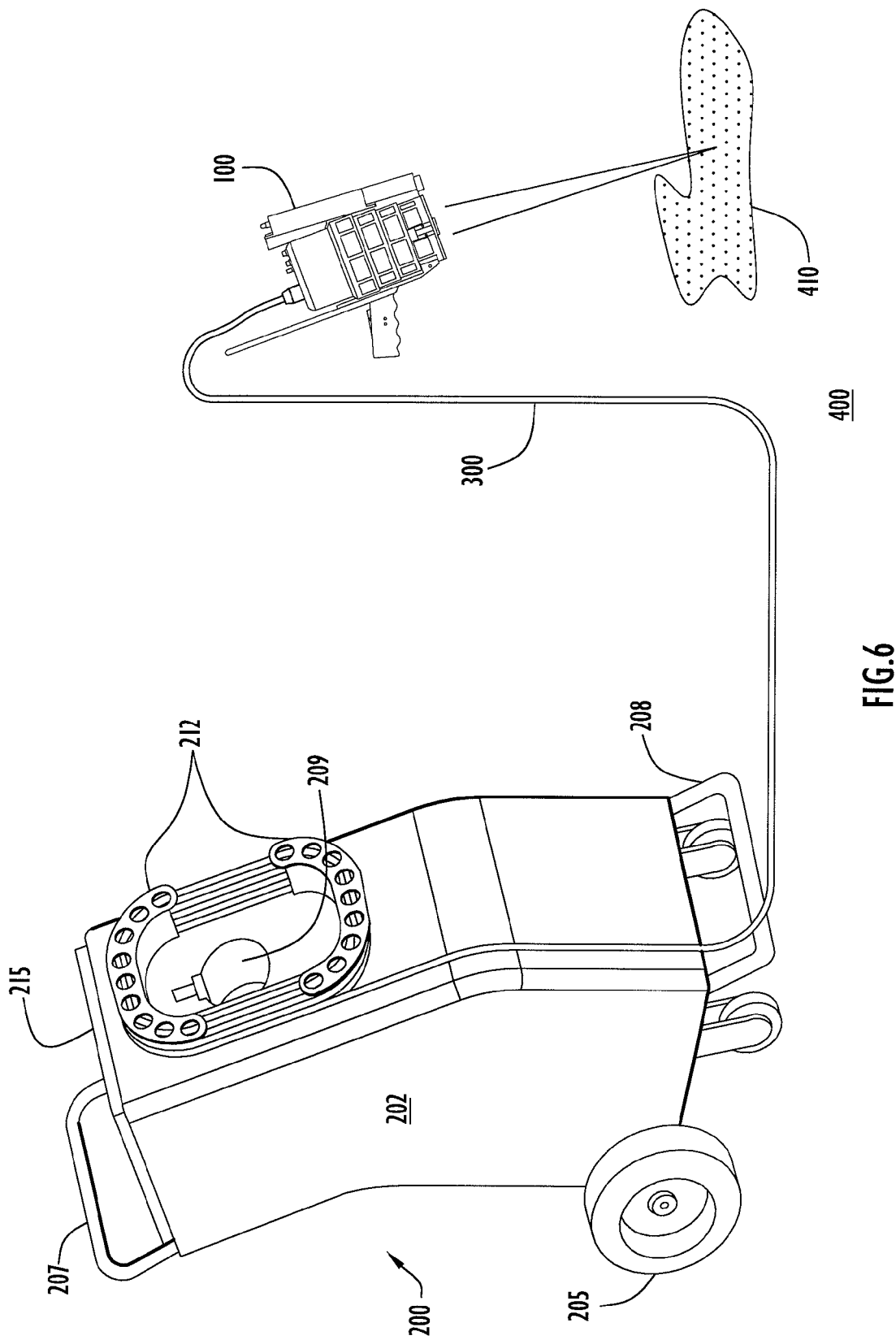
FIG. 6 is a perspective view of a standoff surface-hazard detection system according to an embodiment of the invention.

FIG. 6 shows the processing unit 200 in the form of a cart comprising a housing 202, one or more wheels 205 attached to the housing 202 and a handle 207 to allow a person to move the processing unit 200. The housing 202 may further comprise feet 208 that are used to keep the processing unit 200 stable. The housing 202 further comprises a receptacle 209 to store the hand-held unit 100 when not in use. There are brackets 212 to wrap the cable 300 around when the system is not in use, or to take up extra-slack in the cable 300 when the system is in use.

With reference to FIG. 6, operation of one embodiment of the system 10 will be described. The system 10 can be used by one person or two-persons. A two-person deployment involves a first person attending to the processing unit 200 and a second person using the hand-held unit 100. The person operating the hand-held unit 100 approaches a surface 400 on which there is a solid or liquid substance 410 to be interrogated. This person moves the hand-held unit 100 over the surface 400 and uses the beams emitted by the diodes 117 to focus by moving the hand-held unit 100 towards or away from the surface 400 so that the beams from the diodes 117 intersect or nearly intersect on the surface 400 at a focal point of the collection optics 120. By using a focal distance of approximately one meter, the resulting depth of field of the collection telescope for 70% collection is on the order of about two inches in either direction of the focal point, such that the interrogating light beam from the laser in the hand-held unit 100 can be moved (scanned) across easily without coming out of focus. After the user has positioned the hand-held unit 100 in focus on the surface 400, the laser is activated and the returned optical energy is collected by the hand-held unit 100 and coupled via the fiber optical bundle in the umbilical cable 300 to the processing unit 200. The processing unit 200 analyzes the returned optical energy and generates for display data describing the nature of the detected substance. In addition, the processing unit 200 may generate a trigger signal that is coupled to the alarm device in one or both of the processing unit 200 and the hand-held unit 100 when the detected substance is of a harmful type to activate an audible and/or visual alert notification to the users. This will alert the users to exercise great caution when conducting further investigation, and/or to leave the area immediately. There may be different levels of alarms that are generated by the processing unit 200 depending on the degree of hazard associated with the detected substance.

As an alternative to the configuration shown in FIG. 6, the hand-held unit 100 may be attached to a distal end of a mechanical arm device 500 as shown in FIG. 4B. The arm device 118 comprises a proximal end and a distal end and may incorporate free-space optical coupling of light between the first and second units. The proximal end of the arm device 118 attaches to the top of the processing unit 200 in the form shown in FIG. 6, and the hand-held unit 100 attaches to the distal end of the arm device 118. The mechanical arm device 500 may be remotely controlled from the processing unit 200 to direct the hand-held unit 100 towards a desired surface to interrogate that surface.

Figure 7:
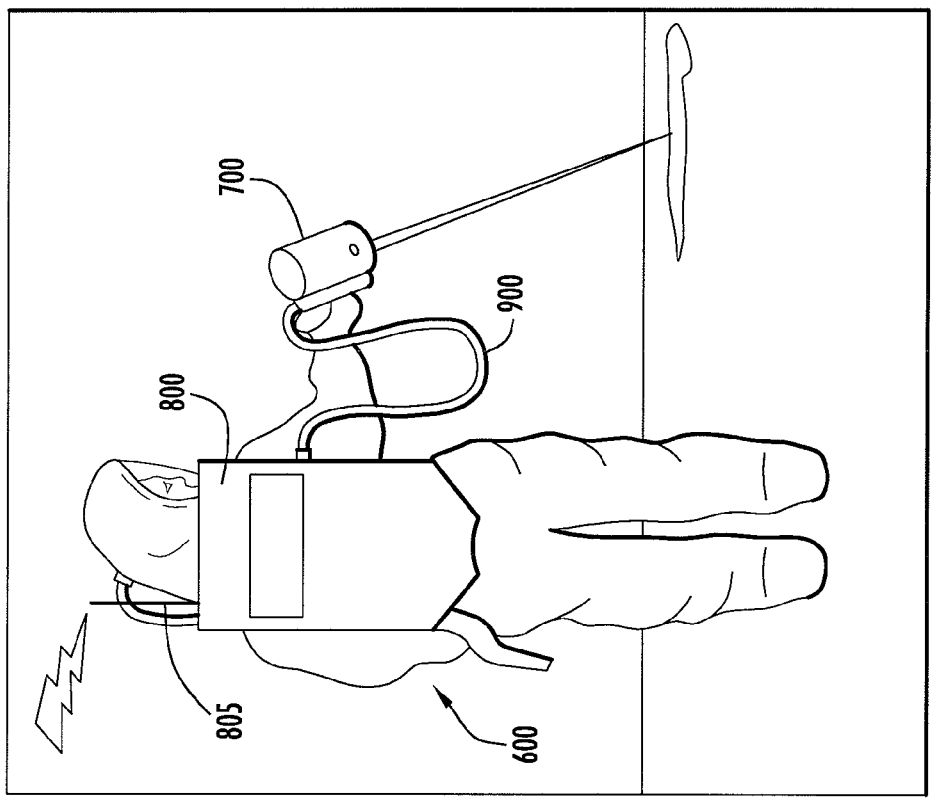
FIG. 7 is a diagram showing operation of the standoff hazard detection system according to the embodiment of the invention shown in FIG. 3.
Figure 7:
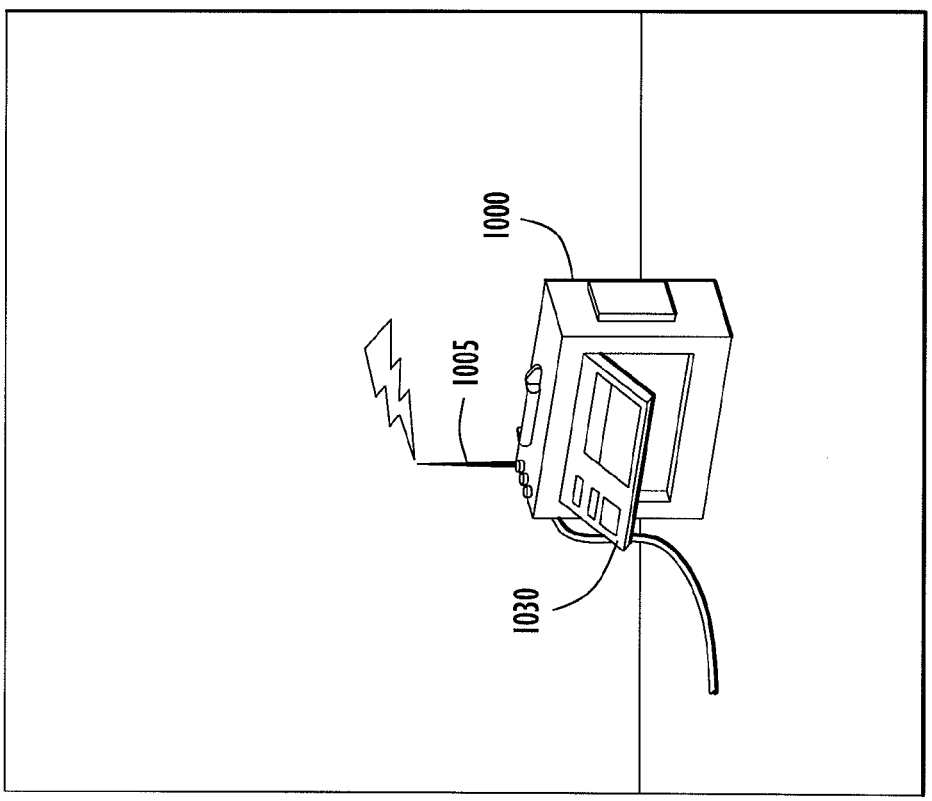

With reference to FIG. 7, operation is now described of the man-portable assembly 600 and base station 1000 described above in connection with FIG. 3. The body-wearable unit 800 is contained within a wearable apparatus or housing, such as a backpack. Alternatively, the wearable apparatus 800 may take other forms such as head-wearable, arm-wearable, waist-wearable (waist pack), etc. An umbilical cable 900 connects the handheld unit 700 to the wearable unit 800. The man-portable assembly 600 has some processing capability and communicates via a link, such as a wireless link, to the remote base station 1000 where more extensive processing may be performed. Generally, to reduce the weight and bulkiness of the equipment that a user must wear, the body-wearable unit 800 may include a spectrograph for processing the returned optical energy signals as well as some processing capability, but the complete data processing is performed at the remote base station 1000. The wearable unit 800 may be designed to be light, such as less than about 20 kg (45 lbs).

Figure 8:
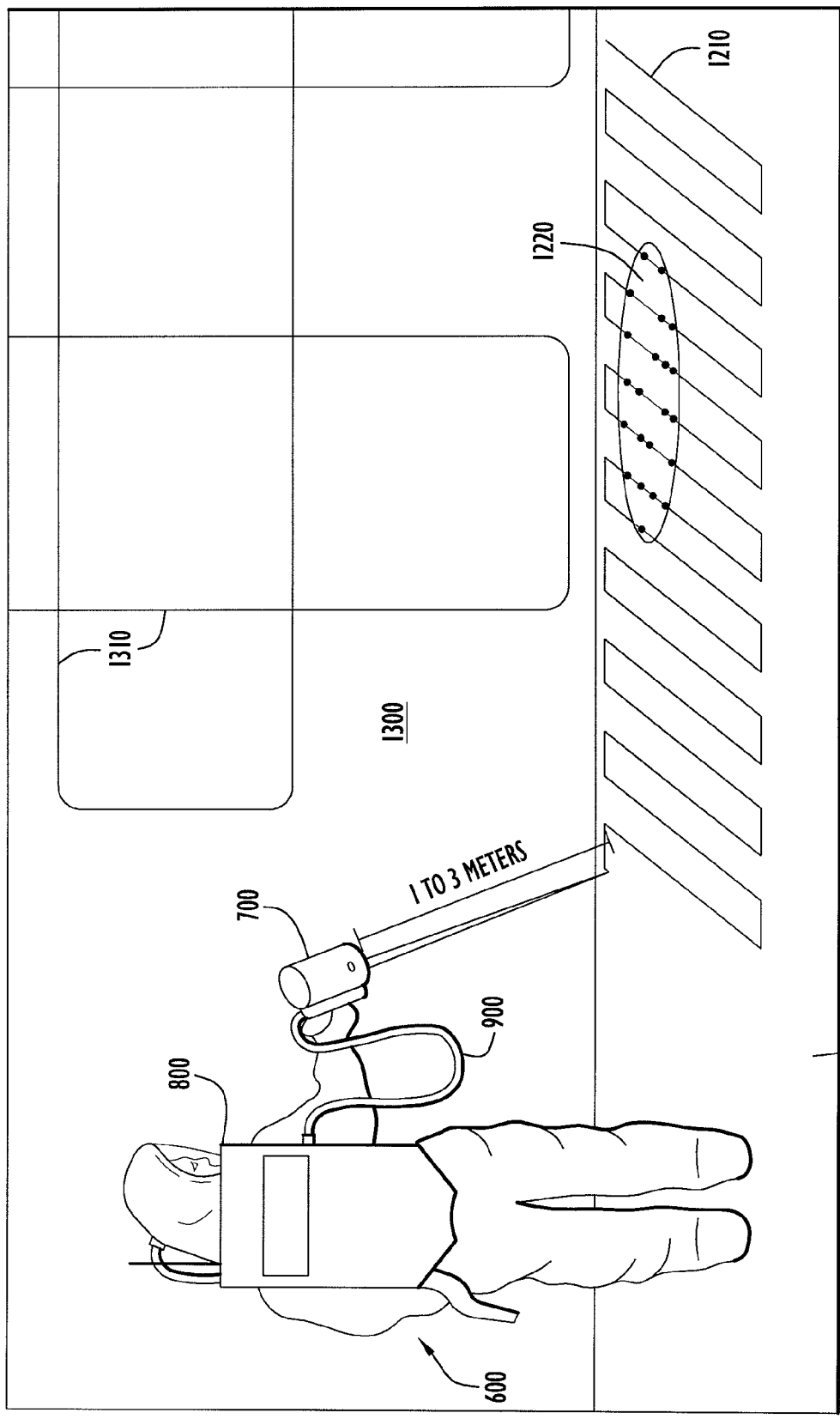
FIG. 8 is a diagram illustrating a use-scenario of the standoff hazard detection system for scanning various surfaces and searching contamination patches according to an embodiment of the invention.

FIG. 8 illustrates an example of the type of scenario for which the system shown in FIG. 7 may be used. A possible hazard or contamination is determined to exist at a site (indoors or outdoors). A responder puts on the man-portable assembly 600 and one or more base stations 1000(1) to 1000 (N) is/are positioned a safe distance from the suspected hazard, e.g., outside a contaminated building or on a different floor. The responder individuals, who may be wearing protective gear and the man-portable assembly 600 go to the suspected hazard-contaminated scene. There may be multiple persons that are each deployed with the man-portable assembly 600. Each man-portable assembly 600 communicates with one or more of the base stations 1000(1) to 1000(N). The hand-held unit 700 is used to interrogate the suspected surface at a standoff of at least about 1 meter without coming into contact with the suspected surface or object. The man-portable assembly 600 transmits spectrum data concerning the interrogated surface to the base station for processing. If the base station 1000($i$) (or man-portable assembly 600) detects a surface contamination, the substance is identified and the base station may transmit a signal to the man-portable assembly 600 in a relatively short time (e.g., within a few seconds or less) with a relatively high degree of confidence. The responder may proceed to map the detected hazardous substance, taking advantage of the high flexibility of line of sight. The coordinated hazard detection and identification system depicted in FIGS. 7 and 8 allows for a central (scene) control station to coordinate a detection sweep of surfaces in a region of interest.

FIG. 8 also shows graphical element lines to indicate where in the scene the detector has already scanned for substances. For example, on the horizontal surface 1200 (e.g., the ground), graphical element lines 1210 indicate where the detector has already scanned on the surface 1200. A hazardous substance detection patch is shown at reference numeral 1220. Similarly, on a vertical surface 1300 (e.g., a wall), graphical element lines 1310 are drawn to indicate where on the vertical surface 1300 the detector has already scanned Another physical platform that may be useful to deploying the stand-off detection technology is a manned ground vehicle or an unmanned mobile ground vehicle. The feature and functions of the man-portable assembly 600 can be integrated or mounted in either type of vehicle. The advantage of deploying the technology in an unmanned mobile ground vehicle is that the vehicle can capture spectrum data for analysis by the vehicle or by a remote base station so that a person does not need to come in proximity to a potentially hazardous substance.

The system and methods described herein may be embodied in other specific forms without departing from the spirit or essential characteristics thereof. The foregoing embodiments are therefore to be considered in all respects illustrative and not meant to be limiting.

What is claimed is:

1. A standoff hazard detection and identification system capable of detecting and identifying contaminants on a surface, comprising:

a first unit that emits a beam of light onto a surface that is located a distance away from the first unit and captures scattered radiation from said surface as a result of said beam of light;

a second unit comprising a spectrograph that converts said scattered radiation to spectral data, wherein the second unit comprises a processor configured to control said second unit to operate in one of first and second modes of operation, where in the first mode, the spectrograph accumulates a relatively small number of returns of scattered radiation for a measurement frame to provide a relatively higher rate for faster scanning on said surface and relatively lower fidelity analysis, and in the second mode, the spectrograph accumulates a relatively high number of returns of scattered radiation for a measurement frame to provide a relatively slower rate for slower scanning on said surface and relatively higher fidelity analysis; and a link between said first unit and said second unit to couple said scattered radiation from said first unit to said second unit.

2. The system of claim 1, wherein said first unit is a portable hand-held device and comprises a light source that produces the beam of light.

3. The system of claim 1, wherein said light source is an ultraviolet (UV) laser.

4. The system of claim 3, wherein said second unit comprises the UV laser and the first unit comprises a final UV-conversion stage that is pumped by the UV laser in the second unit and coupled to the UV laser via an optical fiber that extends along said link from the second unit to the first unit.

5. The system of claim 1, wherein said first unit comprises a collection optics subsystem that collects said scattered radiation from said surface for coupling via said link to said second unit.

6. The system of claim 5, wherein the first unit comprises a housing having a front window sized to support optical elements associated with a laser light source and the collection optics subsystem, the collection optics subsystem comprising a primary mirror and a secondary mirror, wherein the primary minor is fixed and the secondary mirror is movable along an optical axis and wherein the secondary minor is configured to tip and tilt in order to adjust an optical path for the returned optical energy through the collection optics subsystem.

7. The system of claim 6, wherein the second unit comprises a light source that generates the beam of light and an optical fiber coupled between the light source of the second unit and the first unit, and further comprising an articulated arm connected to a base of the housing of the first unit, wherein the articulated arm is configured to tip and tilt the optical axis of the beam of light.

8. The system of claim 5, wherein the second unit comprises a light source that generates the beam of light and an optical fiber coupled between the light source of the second unit and the first unit, wherein the collection optics subsystem comprises a primary minor, a secondary mirror, and a Raman filter that is configured to separate excitation light that is transmitted through the collection optics subsystem from received scattered radiation that in the same optical path as the excitation light, wherein the primary mirror is movable and the secondary mirror is fixed.

9. The system of claim 5, wherein said first unit comprises a visible target indicator that emits a plurality of beams of visible light through said collection optics subsystem so that the plurality of beams intersect each other on said surface at a focal point of said collection optics subsystem.

10. The system of claim 9, wherein said visible target indicator comprises at least two laser diodes mounted on a housing of said first unit, and a dichroic mirror, wherein the laser diodes are pointed inward into the housing to direct their beams to the dichroic minor which is positioned to reflect beams from the diodes into a bore sight of the first unit through which the light beam is to be directed so that the beams from the diodes intersect each other on said surface at a focal point of said collection optics subsystem.

11. The system of claim 1, wherein said light source generates said beam of light in the ultraviolet (UV) spectrum to induce substances on said surface to emit Raman scattered radiation from said surface.

12. The system of claim 11, wherein said processor compares said spectral data to a plurality of spectral data of known substances, and determines whether said substance is a known or foreign substance.

13. The system of claim 11, wherein said first unit is moved across the surface in order to scan the surface at a scanning rate up to tens of centimeters per second.

14. The system of claim 1, wherein said light source generates said beam of light so as to illuminate a spot that is less than one millimeter in diameter.

15. The system of claim 1, wherein said second unit generates data at a rate of more than 10 measurement frames per second.

16. The system of claim 1, wherein said first unit comprises a collection optics subsystem that collects said scattered radiation from said surface for coupling via said link to said second unit, wherein said collection optics subsystem comprises one or more optical elements that are movable to adjust a focal point of said collection optics subsystem.

17. A standoff hazard detection and identification system capable of detecting and identifying contaminants on a surface from a distance, comprising:

a first unit comprising a light source that emits a beam of light onto a surface that is located a distance away from the first unit and an optical subsystem that captures scattered radiation from said surface as a result of said beam of monochromatic light;

a second unit coupled to said first unit comprising a spectrograph that converts said scattered radiation to spectral data and a processor that analyzes said spectral data in order to detect a contaminant on said surface, said second unit comprising a wireless transceiver configured to wirelessly transmit over the air said spectral data to another device for processing; and a third unit physically separate from the first unit and second unit and comprising a wireless transceiver that is configured to receive said spectral data from said second unit and a processor that is configured to analyze said spectral data with one or more algorithms that are more computationally intensive than algorithms used by the processor in said second unit;

wherein said processor in said second unit is configured to control said second unit to operate in one of first and second modes of operation, where in the first mode, the spectrograph accumulates a relatively small number of returns of scattered radiation for a measurement frame to provide a relatively higher rate for faster scanning on said surface and relatively lower fidelity analysis, and in the second mode, the spectrograph accumulates a relatively high number of returns of scattered radiation for a measurement frame to provide a relatively slower rate for slower scanning on said surface and relatively higher fidelity analysis.

18. The system of claim 17, wherein said wireless transceiver in the third unit transmits to said second unit results of analysis performed by the processor in said third unit.

19. The system of claim 18, wherein said second unit comprises a user interface and display to display said results.

20. The system of claim 17, wherein second unit comprises a rechargeable power supply, and said third unit comprises a docking port to connect to said second unit in order to exchange information with said second unit, and for supplying electrical energy to charge said rechargeable power supply chargeable batteries of said second unit.

21. A standoff hazard detection system, comprising:

a light source that emits a beam of light onto a surface to excite Raman scattered radiation from said surface;

an optical subsystem that collects the Raman scattered radiation;

a spectrograph that receives the Raman scattered radiation collected by said optical subsystem and generates a measurement frame of Raman spectral data based on an accumulation of a plurality of returns of Raman scattered radiation from said surface; and a processor that analyzes the Raman spectral data using Raman spectroscopy techniques to discriminate substances on said surface, wherein the processor is configured to control the spectrograph in one of first and second modes, wherein in the first mode, the processor controls the spectrograph to accumulate a relatively small number of returns of scattered radiation for a measurement frame to provide a relatively higher rate for faster scanning on the surface and lower fidelity analysis, and in the second mode, the processor controls the spectrograph to accumulate a relatively high number of returns of scattered radiation for a measurement frame to provide a relatively slower rate for slower scanning of the surface and higher fidelity analysis.

22. A method for standoff detection of a hazardous substance, comprising:

in a first hand-held unit, directing a light beam to a surface located a distance away from the first unit;

in said first unit, capturing returned scattered radiation from said surface as a result of interaction of the light beam with a substance on said surface;

coupling said returned scattered radiation to a second unit separate from said first unit;

generating spectral data from said returned scattered radiation in said second unit in one of first and second modes, wherein in the first mode, generating comprises generating said spectral data from accumulation of a relatively small number of returns of scattered radiation for a measurement frame to provide a relatively higher rate for faster scanning on the surface and lower fidelity analysis, and in the second mode, generating comprises generating said spectral data from accumulation of a relatively high number of returns of scattered radiation for a measurement frame to provide a relatively slower rate for slower scanning of the surface and higher fidelity analysis; and analyzing said spectral data to detect a contaminant on said surface.

23. The method of claim 22, wherein said analyzing is performed in said second unit.

24. The method of claim 22, and further comprising wirelessly transmitting said spectral data from said second unit to a third unit positioned remotely from said second unit, and wherein said analyzing is performed in said third unit.

25. A man-portable standoff hazard detection apparatus, comprising:

a hand-held unit that directs a light beam onto a surface located a distance away from the hand-held unit and an optical subsystem that captures returned scattered radiation from said surface as a result of said light beam;

a body wearable unit comprising a spectrograph that generates spectral data from the returned scattered radiation, wherein said spectrograph comprises a processor configured to control said second unit to operate in one of first and second modes of operation, where in the first mode, the spectrograph accumulates a relatively small number of returns of scattered radiation for a measurement frame to provide a relatively higher rate for faster scanning on said surface and lower fidelity analysis, and in the second mode, the spectrograph accumulates a relatively high number of returns of scattered radiation for a measurement frame to provide a relatively slower rate for slower scanning on said surface and higher fidelity analysis; and a cable that connects said hand-held unit to said wearable unit, wherein said cable comprises one or more optical fibers that transports said returned scattered radiation collected by said optical subsystem in said hand-held unit to said spectrograph in said wearable unit.

26. The apparatus of claim 25, wherein said processor of the body wearable unit analyzes said spectral data using spectroscopy techniques to identify a substance on said surface.

27. The apparatus of claim 26, and further comprising a display device in said body wearable unit that is connected to said processor to display information for a substance determined to be present on said surface.

28. The system of claim 25, and further comprising a plurality of hazard detectors each comprising a hand-held unit and an associated body wearable unit, and a central control station wirelessly linked to the plurality of hazard detectors, wherein the central control station is configured to receive detection and identification data from said plurality of hazard detectors and to transmit control signals to the plurality of hazard detectors in order to coordinate a detection sweep of surfaces in a region of interest by the plurality of hazard detectors.

29. The system of claim 28, and further comprising a plurality of base stations connected by a wired network to the central control station, and wherein each base station comprises a radio frequency (RF) transceiver configured to send RF signals to a hazard detector and to receive RF signals from a hazard detector, and wherein the central control station sends the control signals to one or more base stations which in turn wirelessly transmit the control signals as RF signals to one or more hazard detectors.

30. The system of claim 29, wherein each base station further comprises a processor that is configured to analyze spectral data sent via RF signals to the base station from a hazard detector, and wherein the processor in each base station is configured to analyze the spectral data with one or more algorithms that are more computationally intensive than algorithms used by the processor in the body wearable unit of a hazard detector.

* * * * *